(12) United States Patent
Lee (10) Patent No.: US 10,041,032 B2
(45) Date of Patent: Aug. 7, 2018

(54) SIMPLE ANIMAL CELL CULTURE DEVICE AND METHOD FOR CULTURING ANIMAL CELLS USING SAME

(71) Applicant: KOREA INSTITUTE OF INDUSTRIAL TECHNOLOGY, Cheonan-si, Chungcheongnam-do (KR)

(72) Inventor: Woo-Jong Lee, Cheonan-si (KR)

(73) Assignee: KOREA INSTITUTE OF INDUSTRIAL TECHNOLOGY, Cheonan-si, Chungcheongnam-Do (KR)

( * ) Notice: Subject to any disclaimer, the term of this patent is extended or adjusted under 35 U.S.C. 154(b) by 322 days.

(21) Appl. No.: 14/891,149

(22) PCT Filed: Jun. 26, 2014

(86) PCT No.: PCT/KR2014/005671
§ 371 (c)(1),
(2) Date: Nov. 13, 2015

(87) PCT Pub. No.: WO2015/008949
PCT Pub. Date: Jan. 22, 2015

(65) Prior Publication Data
US 2016/0108351 A1    Apr. 21, 2016

(30) Foreign Application Priority Data
Jul. 18, 2013 (KR) ........................ 10-2013-0084575

(51) Int. Cl.
*C12M 1/12*     (2006.01)
*C12M 1/00*     (2006.01)

(52) U.S. Cl.
CPC ............ *C12M 25/00* (2013.01); *C12M 23/06* (2013.01); *C12M 23/38* (2013.01); *C12M 25/02* (2013.01); *C12M 25/14* (2013.01)

(58) Field of Classification Search
CPC ...... C12M 23/06; C12M 23/38; C12M 25/14; C12M 25/00; C12M 25/02
See application file for complete search history.

(56) References Cited

U.S. PATENT DOCUMENTS

| | | | |
|---|---|---|---|
| 5,270,207 A | * | 12/1993 | Matsumura et al. ............. B01F 13/0818 435/295.1 |
| 2006/0228265 A1 | * | 10/2006 | Peng et al. .......... B01L 3/50255 422/400 |
| 2007/0042454 A1 | * | 2/2007 | Nix ........................ C12M 23/08 435/34 |
| 2010/0203638 A1 | | 8/2010 | Adachi et al. |

FOREIGN PATENT DOCUMENTS

| | | |
|---|---|---|
| JP | 2000-157261 A | 6/2000 |
| JP | 2004-222545 A | 8/2004 |
| JP | 4671365 B2 | 4/2011 |
| KR | 10-0679112 B1 | 2/2007 |
| KR | 10-2009-0059448 A | 6/2009 |
| KR | 10-2009-0065643 A | 6/2009 |

* cited by examiner

*Primary Examiner* — Gautam Prakash
(74) *Attorney, Agent, or Firm* — Rabin & Berdo, P.C.

(57) ABSTRACT

The present invention relates to a simple animal cell culture device and a method for culturing animal cells using the same, and provides a simple animal cell culture device comprising: a culture vessel for holding a culture medium; an animal cell reservoir coupled to the upper portion of the culture vessel; a cell support housed on the inside of the animal cell reservoir and having animal cells adhered thereto; and a cover for covering the top of the culture vessel.

19 Claims, 6 Drawing Sheets

SIMPLE ANIMAL CELL CULTURE DEVICE AND METHOD FOR CULTURING ANIMAL CELLS USING SAME

TECHNICAL FIELD

The present disclosure relates to an animal cell culture device and a method for culturing animal cells using the same, and more particularly, to a simple animal cell culture device capable of not only concentrated-culture of animal cells to high concentration, but also concentrating effective proteins such as cell growth promoting factors, or target protein, and an animal cell culturing method thereof.

BACKGROUND ART

Certain methods that produce target proteins with cell culture uses animal cells. The quantity of target proteins produced by way of animal cell culture is determined by multiplication of the number of cells by the quantity of proteins produced per unit cell. Accordingly, in order to increase production quantity of the target proteins, it is necessary to adopt a method such as high concentrated cell culture which increases the number of animal cells for producing proteins, or a method of increasing proteins per unit cells.

When it comes to high-concentration cell culture, optimized culture composition is most important for the growth of animal cells, and frequent medium change is particularly required.

Meanwhile, Korean Registered Patent No. 10-0679112 (entitled 'Animal cell culture method') is a patent document proposing animal cell culture. The animal cell culture device disclosed in the above-mentioned document can be used for the culture of animal cells, but has a shortcoming. That is, the complicated structure results in increased overall volume, which is inadequate for the purpose of simple animal cell culture.

In order to address the shortcoming mentioned above, Korean Patent Publication No. 10-2009-0059448 suggests "Portable small-sized animal cell culture device and a manufacturing method thereof". However, the proposed portable small-sized animal cell culture device has a shortcoming in that frequent medium change is not allowed.

Frequent medium change is required, since the animal cells are concentrated and cultured when inducing cultivation of the high-concentration animal cells. However, the conventional portable small-sized animal cell culture device has a difficulty of frequent medium change, and during medium change, effective proteins such as growth promoting factors or target proteins already grown by the animal cells also drain out and diluted, which is the result contrary to the desired result, i.e., the increased production quantity of target proteins.

DISCLOSURE OF INVENTION

Technical Problem

An object of the present disclosure is to solve the problems mentioned above, and accordingly, it is an object of the present disclosure to provide a simple animal cell culture device having a simple structure, which allows convenient culture of animal cells, and a method for culturing animal cells using the same.

Another object of the present disclosure is to provide an animal cell culture device which allows frequent medium change, thus allowing high-concentration cell culture, and a method for culturing animal cells using the same.

Yet another object of the present disclosure is to provide an animal cell culture device capable of preventing external release of effective proteins such as growth promoting factors or target proteins during medium change, and a method for culturing animal cells using the same.

The abovementioned objects and other advantages of the present disclosure will be elucidated herein for those skilled in the art, by referring to preferred exemplary embodiments of the present disclosure.

Solution to Problem

According to the present disclosure, a simple animal cell culture device includes a culture vessel for holding a culture medium; an animal cell reservoir coupled to an upper portion of the culture vessel; a cell support housed inside the animal cell reservoir and to which animal cells are adhered; and a cover for covering the upper portion of the culture vessel.

According to an embodiment, the animal cell reservoir is so configured that the animal cells and proteins therein are not allowed to be discharged outside, while nutrient ingredients and waste are allowed to be discharged outside.

According to an embodiment, the animal cell reservoir is so configured that the animal cells therein are not allowed to be discharged outside, while proteins, nutrient ingredients and waste are allowed to be discharged outside.

According to an embodiment, the animal cell reservoir is formed of any one of semi-permeable film, mesh net, non-woven fabric material and woven fabric material.

According to an embodiment, the animal cell reservoir includes a reservoir body for housing the animal cells therein; and a coupling frame extending on an upper portion of the reservoir body externally in a radial direction, and locked with the upper portion of the culture vessel, wherein a plurality of micro holes are pierced through a plate surface of the reservoir body, to allow the culture medium to be introduced and discharged therethrough.

According to an embodiment, a medium introducing pipe extends from a lower portion of the culture vessel to a predetermined length, to allow the medium to be introduced from outside therethrough.

According to an embodiment, a culture medium discharge pipe extends from the upper portion of the culture vessel to a predetermined length, to allow the culture medium to be discharged from inside to outside.

According to an embodiment, an inlet is pierced through a surface of the cover to allow carbon dioxide to be introduced therethrough into the culture vessel.

According to an embodiment, an antibacterial filter is provided between the cover and the culture vessel to remove germs contained in the carbon dioxide introduced through the cover.

According to an embodiment, the cell support is formed as a lattice-shaped porous structure.

According to an embodiment, the cell support is formed as a three-dimensional structure.

According to an embodiment, a first screw thread is provided on an outer circumference of an upper area of the culture vessel, a lower area is formed as a conical shape, and a second screw thread is provided on an inner side surface of the cover, for screw-coupling with the first screw thread.

Meanwhile, the present disclosure provides an animal cell culture method, including: filling a simple animal cell culture device with a medium, in which the simple animal cell culture device includes a culture vessel for holding a culture medium, an animal cell reservoir coupled to an upper portion of the culture vessel, a cell support housed inside the animal cell reservoir and to which animal cells are adhered, and a cover for covering the upper portion of the culture vessel; and settling the cell support with the animal cells adhered thereto in the animal cell reservoir, for culture thereof. In this case, preferably, according to elapse of an animal cell culture time, the culture vessel cover may be opened and the medium may be changed, repeatedly.

Further, the present disclosure provides an animal cell culture method, including: filling a simple animal cell culture device with a medium, in which the simple animal cell culture device includes a culture vessel for housing a culture medium, an animal cell reservoir coupled to an upper portion of the culture vessel, a cell support housed inside the animal cell reservoir and to which animal cells are adhered, and a cover for covering the upper portion of the culture vessel, and additionally includes a medium introducing pipe extending from a lower portion of the culture vessel to a predetermined length, to allow the medium to be introduced from outside therethrough, and a culture medium discharge pipe extending from the upper portion of the culture vessel to a predetermined length, to allow the culture medium to be discharged from inside to outside; and settling the cell support with the animal cells adhered thereto in the animal cell reservoir, for culture thereof. In this case, according to elapse of an animal cell culture time, the medium may preferably be changed repeatedly, by use of the medium introducing pipe and the culture medium discharge pipe.

Further, the present disclosure provides an animal cell culture method, including: filling a simple animal cell culture device with a medium, in which the simple animal cell culture device includes a culture vessel for housing a culture medium, an animal cell reservoir coupled to an upper portion of the culture vessel, a cell support housed inside the animal cell reservoir and to which animal cells are adhered, and a cover for covering the upper portion of the culture vessel, and in which an inlet is pierced through a surface of the cover to allow carbon dioxide to be introduced therethrough into the culture vessel; and settling the cell support with the animal cells adhered thereto in the animal cell reservoir, for culture thereof. In this case, the medium may preferably be adjusted in its pH, as carbon dioxide is supplied through the inlet formed in the cover of the culture vessel.

Further, the present disclosure provides an animal cell culture method, including: filling a simple animal cell culture device with a medium, in which the simple animal cell culture device includes a culture vessel for housing a culture medium, an animal cell reservoir coupled to an upper portion of the culture vessel, a cell support housed inside the animal cell reservoir and to which animal cells are adhered, and a cover for covering the upper portion of the culture vessel, and additionally includes a medium introducing pipe extending from a lower portion of the culture vessel to a predetermined length, to allow the medium to be introduced from outside therethrough, and a culture medium discharge pipe extending from the upper portion of the culture vessel to a predetermined length, to allow the culture medium to be discharged from inside to outside, and in which an inlet is pierced through a surface of the cover to allow carbon dioxide to be introduced therethrough into the culture vessel; and settling the cell support with the animal cells adhered thereto in the animal cell reservoir, for culture thereof. In this case, the medium may preferably be adjusted in its pH, as carbon dioxide is supplied through an inlet formed in the culture vessel cover.

Advantageous Effects of Invention

The simple animal cell culture device according to the present disclosure has a small-sized and simple structure, thus allowing convenience of use.

Further, high-concentration animal cell culture is enabled, since external release of effective proteins such as animal cells, growth promoting factors, or target proteins is prevented during medium change.

Further, frequent medium change is enabled, since it is possible to change medium and culture medium independently, through medium introducing pipe and culture medium discharge pipe.

Further, culture medium can be maintained at appropriate pH, since it is possible to supply carbon dioxide, as necessary, through an inlet of a cover.

| <Description of reference numerals> | |
|---|---|
| 100: simple animal cell culture device | |
| 110: culture vessel | |
| 111: vessel body | 111a: first screw thread |
| 113: medium introducing pipe | |
| 115: culture medium discharge pipe | |
| 120: animal cell reservoir | 121: reservoir body |
| 121a: micro holes | 123: coupling frame |
| 130: cell support | 131: lateral support |
| 133: vertical support | |
| 135: perpendicular support | |
| 140: cover | 141: cover body |
| 141a: second screw thread | 143: inlet |
| 150: antibacterial filter | |

MODE FOR THE INVENTION

The preferred embodiments will be explained in greater detail below with reference to the drawings attached hereto. The embodiments of the present disclosure may have a variety of modifications. Accordingly, the scope of the present disclosure should not be limited to the embodiments described in detail below. The embodiments are provided herein to more fully explain the present disclosure for understanding of those with average knowledge in the pertinent art. Accordingly, certain elements may be exaggerated in their shapes or the like in the drawings for increased clarity of the explanation. Note that the same elements in the respective drawings may be referred to by the same reference numerals. The known functions and constitutions may not be described in detail herein, when determined that these may obscure the concept of the present disclosure.

Figure 1:
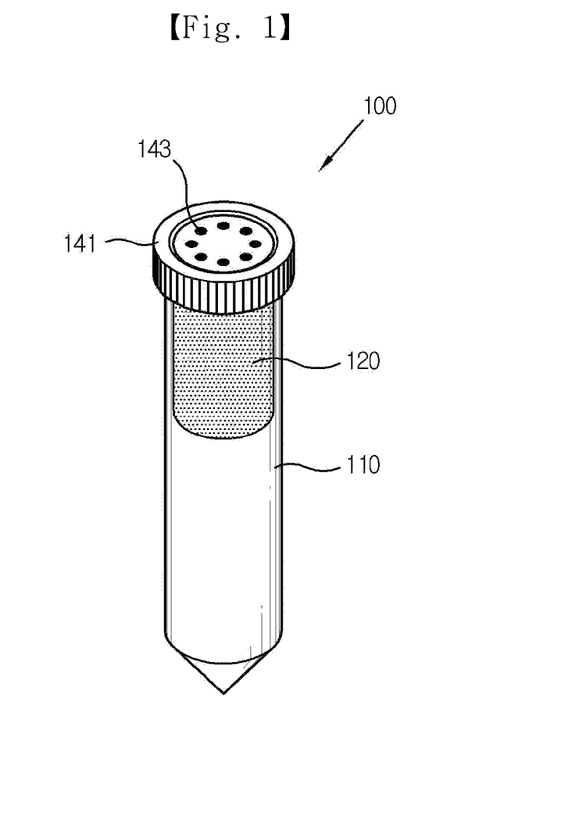
FIG. 1 is a perspective view illustrating a constitution of a simple animal cell culture device according to a preferred embodiment of the present disclosure.
Figure 2:
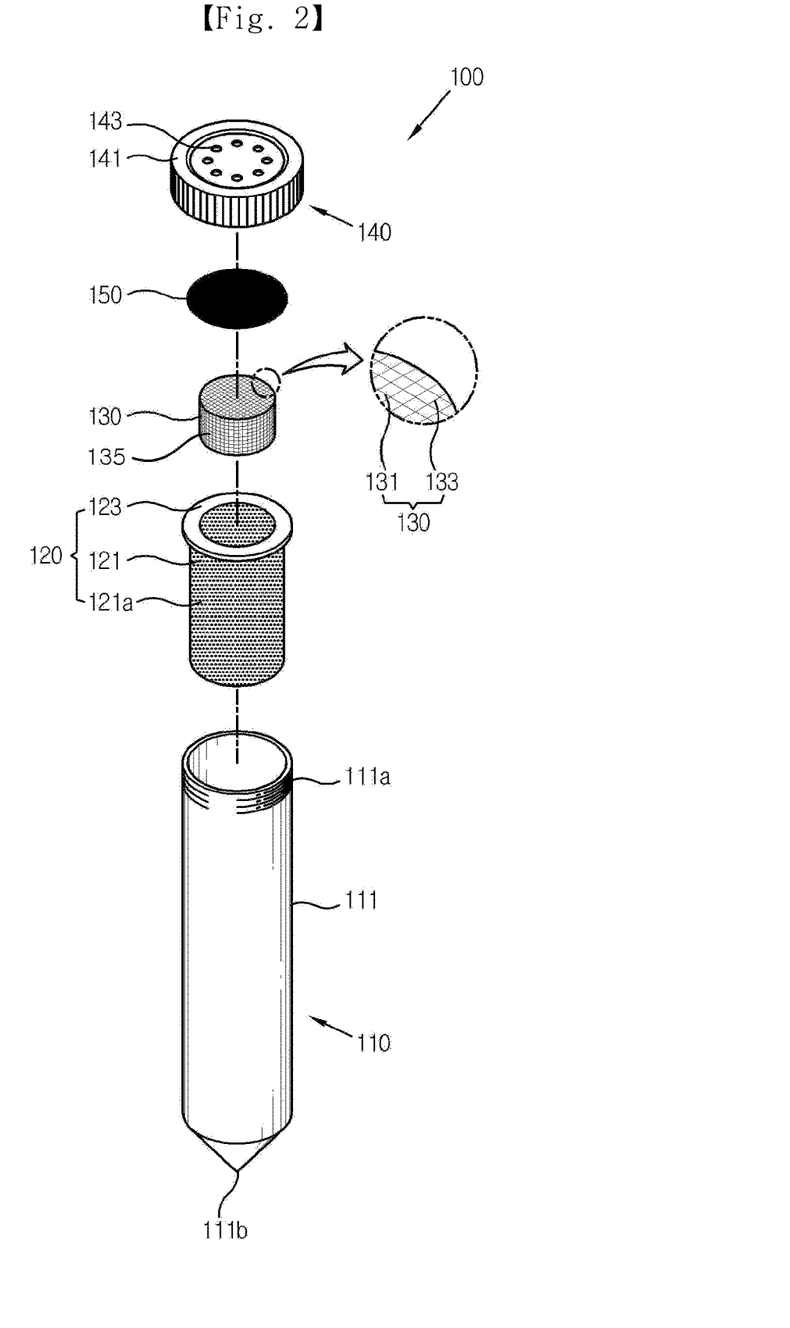
FIG. 2 is an exploded perspective view illustrating a constitution of a simple animal cell culture device according to a preferred embodiment of the present disclosure.

FIG. 1 is a perspective view illustrating a constitution of a simple animal cell culture device 100 according to a preferred embodiment of the present disclosure, and FIG. 2 is an exploded perspective view illustrating a constitution of the simple animal cell culture device 100.

As illustrated, the simple animal cell culture device 100 according to a preferred embodiment of the present disclosure includes a culture vessel 110 holding therein culture medium A, an animal cell reservoir 120 coupled to an upper end of the culture vessel 110, a cell support 130 which is housed inside the animal cell reservoir 120 and on which animal cells M are settled and grown, a cover 140 coupled to an upper end of the culture vessel 110, and an antibacterial filter 150 disposed between the cover 140 and the animal cell reservoir 120.

Medium is held inside the culture vessel 110. The animal cell reservoir 120 is coupled to the upper portion of the culture vessel 110. The culture vessel 110 is formed as a pipe of a predetermined length. The culture vessel 110 may have a lower portion 111b formed as a pointed pipe as illustrated, and a first screw thread 111a formed on an outer circumference of the upper portion for coupling with the cover 140. The culture vessel 110 may be provided in a variety of sizes depending on use thereof.

The animal cell reservoir 120 is coupled to the upper end of the culture vessel 110 and has a cell support 130 housed therein. The animal cell reservoir 120 prevents discharge of the effective proteins such as animal cells and growth promoting factors, and target proteins along with the culture medium A during medium change.

Meanwhile, depending on needs, it may be necessary to discharge the proteins outside. Accordingly, the animal cell reservoir 120 may be configured so that the animal cells therein are not allowed to be discharged outside, while the proteins, nutrient ingredients and waste are allowed to be discharged outside.

The animal cell reservoir 120 includes a reservoir body 121 housing the cell support 130, and a coupling frame 123 formed on the upper portion of the reservoir body 120 and locked with the upper end of the culture vessel 110.

The reservoir body 121 is provided in such a form that allows introduction and discharge of the culture, nutrient ingredients and waste, while not allowing discharge of the animal cells and effective proteins or the target proteins within the reservoir body 121 to outside. At this time, depending on needs, the reservoir body 121 may be provided in such a form that allows introduction and discharge of the culture, nutrient ingredients, waste and proteins, while not allowing discharge of the animal cells from inside the reservoir body 121 to outside. To this purpose, the reservoir body 121 may be provided as a semi-transparent film material or a mesh net, or formed of non-woven fabric material or woven fabric material. Herein, a plurality of micro holes 121a are formed on a plate surface of the reservoir body 121 to allow efficient introduction and discharge of the culture medium. The micro holes 121a are formed in a smaller size than the proteins and animal cells to block the proteins and animal cells from being discharged outside. Further, when necessary, the micro holes 121a may block only the animal cells, while allowing the proteins, culture, nutrient ingredients, waste, and so on to pass therethrough to be discharged outside.

The coupling frame 123 is formed, extending from the upper portion of the reservoir body 121 externally in a radial direction for a predetermined area. The coupling frame 123 supports the animal cell reservoir 120 to be cradled on the upper end of the culture vessel 110 and fixed in position. The coupling frame 123 is formed to have the same outer diameter as that of the culture vessel 110 or shorter by a predetermined length. In this case, the coupling frame 123 has such an outer diameter that it is cradled on the upper portion of the culture vessel 110, and is formed shorter than the inner diameter of the cover 140. Accordingly, it is ensured that no interference is generated in coupling of the cover 140 with the culture vessel 110.

The cell support 130 is housed in the animal cell reservoir 120 to hold therein animal cells so that the animal cells are settled and grown. The cell support 130 is the structure provided to assist adhesion and proliferation of the animal cells. To this end, the cell support 130 is formed into a three-dimensional lattice structure. The cell support 130 constructs a three-dimensional structure consisting of a lateral support 131, a vertical support 133, and a perpendicular support 135 in orthogonal relations to each other.

Animal cells are respectively settled and grown in the porous holes among the lateral support 131, the vertical support 133 and the perpendicular support 135. The cell support 130 may be formed by stacking biodegradable polymer filaments.

The cover 140 is coupled with the upper portion of the culture vessel 110 and seals off the culture vessel 110. The cover 140 includes a cover body 141 covering the upper portion of the culture vessel 110, and a plurality of inlets 143 pierced through the plate surface of the cover body 11 to allow carbon dioxide to flow therethrough to inside. A second screw thread 141a is formed on an inner side of the cover body 141 to correspond to the first screw thread 111a of the vessel body 111. The first screw thread 111a and the second screw thread 141a are formed into female and male screw threads to be screw-coupled with each other.

The inlets 143 supply carbon dioxide into the culture vessel 110. Carbon dioxide prevents abrupt pH variation of the culture medium by the equilibrium with the sodium bicarbonate contained in the medium. Accordingly, carbon dioxide acts as a buffer which adjusts the culture medium to a pH 6.9-7.4 range which is optimal for animal cell growth.

The antibacterial filter 150 is disposed between the cover 140 and the culture vessel 110 to remove various germs included in the inflow of carbon dioxide entering the inlets 143. The antibacterial filter 150 is integrally coupled with an inner side of the cover 140. Accordingly, removing the cover 140 causes the antibacterial filter 150 to be removed together, and coupling the cover 140 to the culture vessel 110 causes the antibacterial filter 150 to be coupled together. Further, as an alternative to the integral type descried above, the antibacterial filter 150 may be cradled on the outer circumference of the animal cell reservoir 120 separately from the cover 140, and then pressed against the inner surface by the coupling force when the cover 140 is screw-coupled with the culture vessel 110, and fixed in position.

Figure 3:
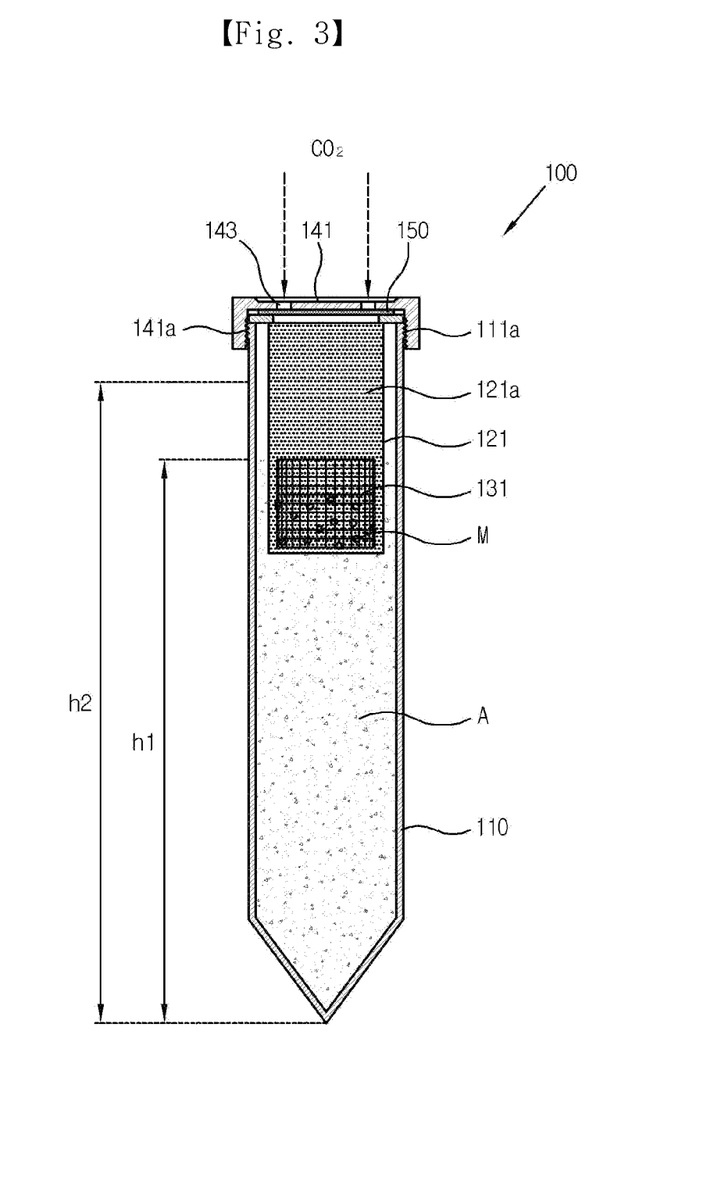
FIG. 3 is a schematic view illustrating a culture process of a simple animal cell culture device according to a preferred embodiment of the present disclosure.

The process of using the simple animal cell culture device 100 in the constitutions as described above according to the preferred embodiments will be described below with reference to FIGS. 1 to 3.

A managing person places the medium inside the culture vessel 110 to a predetermined height, and inserts the animal cell reservoir 120. Inside the animal cell reservoir 120, the cell support 130 with the animal cells M adhered thereto is housed. The cover 140 with the antibacterial filter 150 coupled thereto is coupled with the upper portion of the culture vessel 110. At this time, the medium supplied inside the culture vessel 110 is supplied to height h1, h2 so that the animal cells of the animal cell reservoir 120 are submerged therein.

In this state, the nutrient ingredients within the medium flow into the animal cell reservoir 120 due to semi-permeable property of the animal cell reservoir 120, and contact the animal cells M and used for the growth of the animal cells. Further, the waste of the animal cells M, which is discharged outside the cells as the animal cells grow, is released out of the animal cell reservoir 120 and mixed with the medium. As a predetermined time elapses in that state, the nutrients within the medium are gradually consumed, and the concentration of the waste released from the animal cells increases. After a predetermined period of time since the beginning of culture, the medium turns into the state of a culture medium in which a variety of wastes released from the animal cells are gradually accumulated.

Upon determining that a predetermined time has elapsed since the beginning of the culture so that a large amount of wastes is accumulated and nutrients are used up, the managing person opens the cover 140, grasps the animal cell reservoir 120 with a forcep (not illustrated) and removes the same from the culture vessel 110, and discharges the culture medium with the accumulated waste to outside. The managing person then feeds a fresh medium into the culture vessel 110, couples the animal cell reservoir 120 with the culture vessel 110 again using the forcep (not illustrated), and then closes the cover 140.

In the manner described above, the animal cells, various effective proteins generated from the animal cells, and the target proteins are prevented from discharging outside, during fresh medium change which occurs at predetermined time intervals. As a result, the animal cells and the proteins can be concentrated to a high concentration within the animal cell reservoir 120. Note that, in case there is a need to discharge the proteins to outside, the micro holes 121a may be sized to be larger than the proteins, but smaller than the animal cells, thus blocking the animal cells only, while allowing the proteins and others to be discharged outside.

Figure 4:
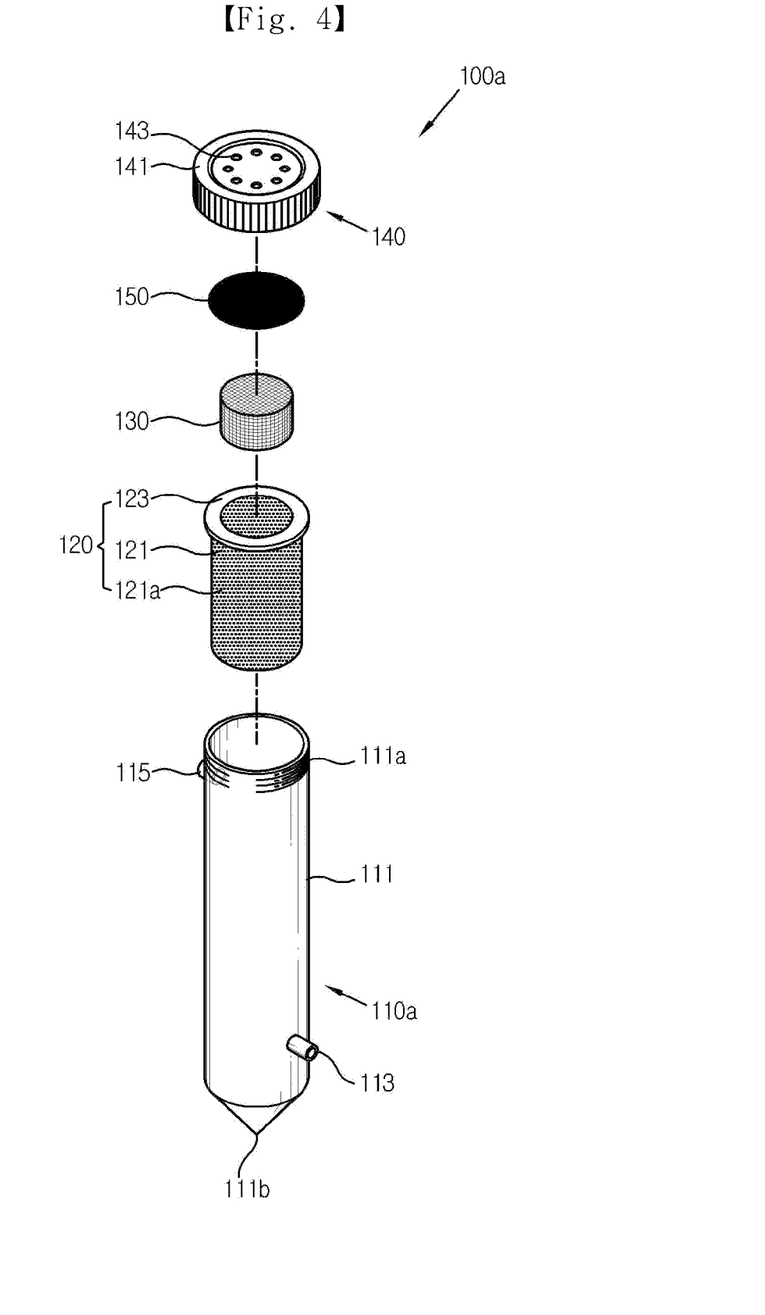
FIG. 4 is an exploded perspective view illustrating a constitution of a simple animal cell culture device according to another embodiment of the present disclosure.
Figure 5:
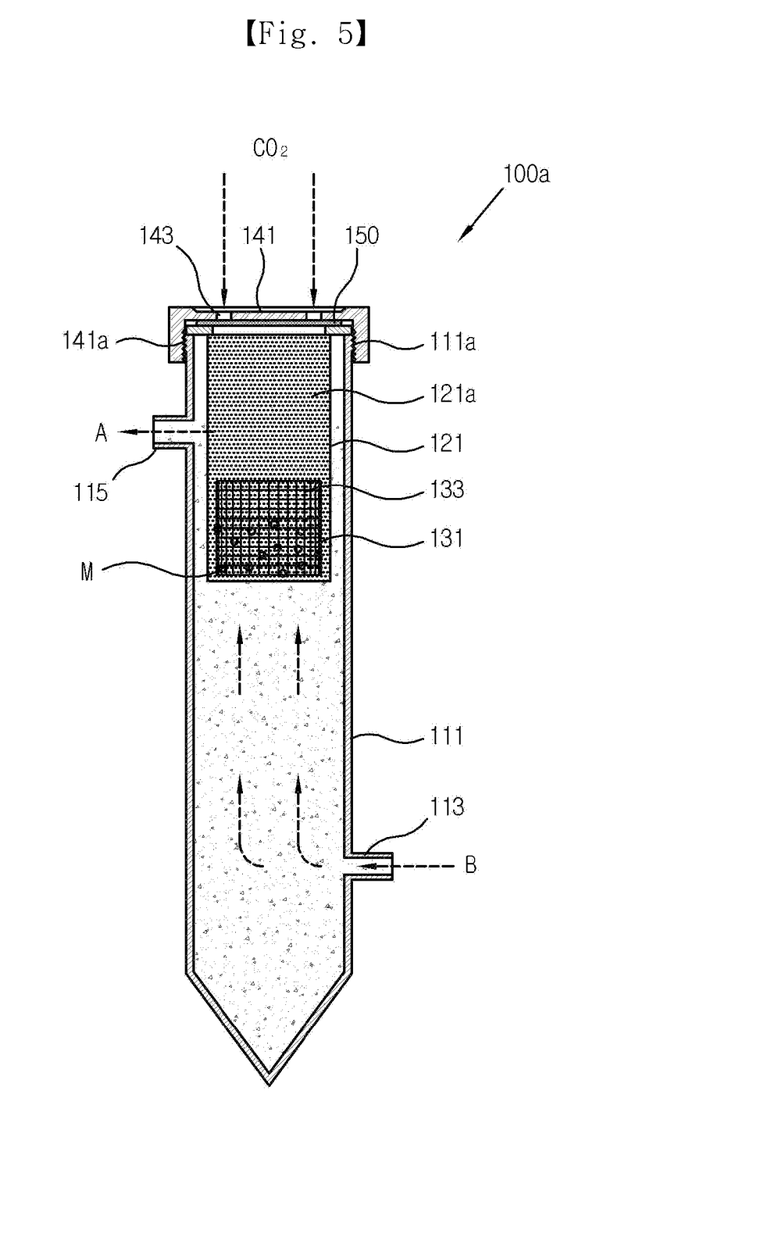
FIG. 5 is a schematic view illustrating a culture process of a simple animal cell culture device according to another embodiment of the present disclosure.

Meanwhile, FIG. 4 is an exploded perspective view illustrating a constitution of a simple animal cell culture device 100a according to another embodiment of the present disclosure, and FIG. 5 is a schematic view illustrating a culture process of a simple animal cell culture device 100a according to another embodiment of the present disclosure.

According to the preferred embodiment of the present disclosure described above, the simple animal cell culture device 100 requires that the cover 140 be separated and the animal cell reservoir 120 be removed to outside in order to change the medium. However, the simple animal cell culture device 100a according to another embodiment of the present disclosure allows to change culture medium and medium while the animal cell reservoir 120 remains being housed inside the culture vessel 110a. To this end, the simple animal cell culture device 100a according to another embodiment of the present disclosure has a medium introducing pipe 113 protruding from a lower portion of the culture vessel 110a to allow the medium B to be introduced therethrough, and a culture medium discharge pipe 115 protruding from an upper portion of the culture vessel 110a to allow the culture medium A to be discharged therethrough to outside. Accordingly, the medium is introduced through the medium introducing pipe 113 of the simple animal cell culture device 100a in a state that the animal cell reservoir 120 is being coupled with the culture vessel 110a of the simple animal cell culture device 100a. At this time, valves may be respectively connected to the medium introducing pipe 113 and the culture medium discharge pipe 115 to open and close medium inflow and culture medium outflow.

When a predetermined time elapses since the animal cell culture begins, and thus it is the time to change the culture medium, a managing person opens the valve (not illustrated) on the side of the culture medium discharge pipe 115 or uses an outflow syringe to cause the culture medium A inside the culture vessel 110a to be discharged outside. When the culture medium inside the culture vessel 110a is completely removed, the managing person opens the valve (not illustrated) on the side of the medium introducing pipe 113 or uses an inflow syringe (not illustrated) to causes fresh medium (B) to be introduced into the culture vessel 110a. At this time, the animal cell reservoir 120 is housed in the culture vessel 110a, but external release of the animal cells and proteins is prevented due to semi-permeable property of the animal cell reservoir 120. Herein, changing the medium and culture medium may be performed independently from each other, or depending on needs, may be performed successively.

Figure 6:
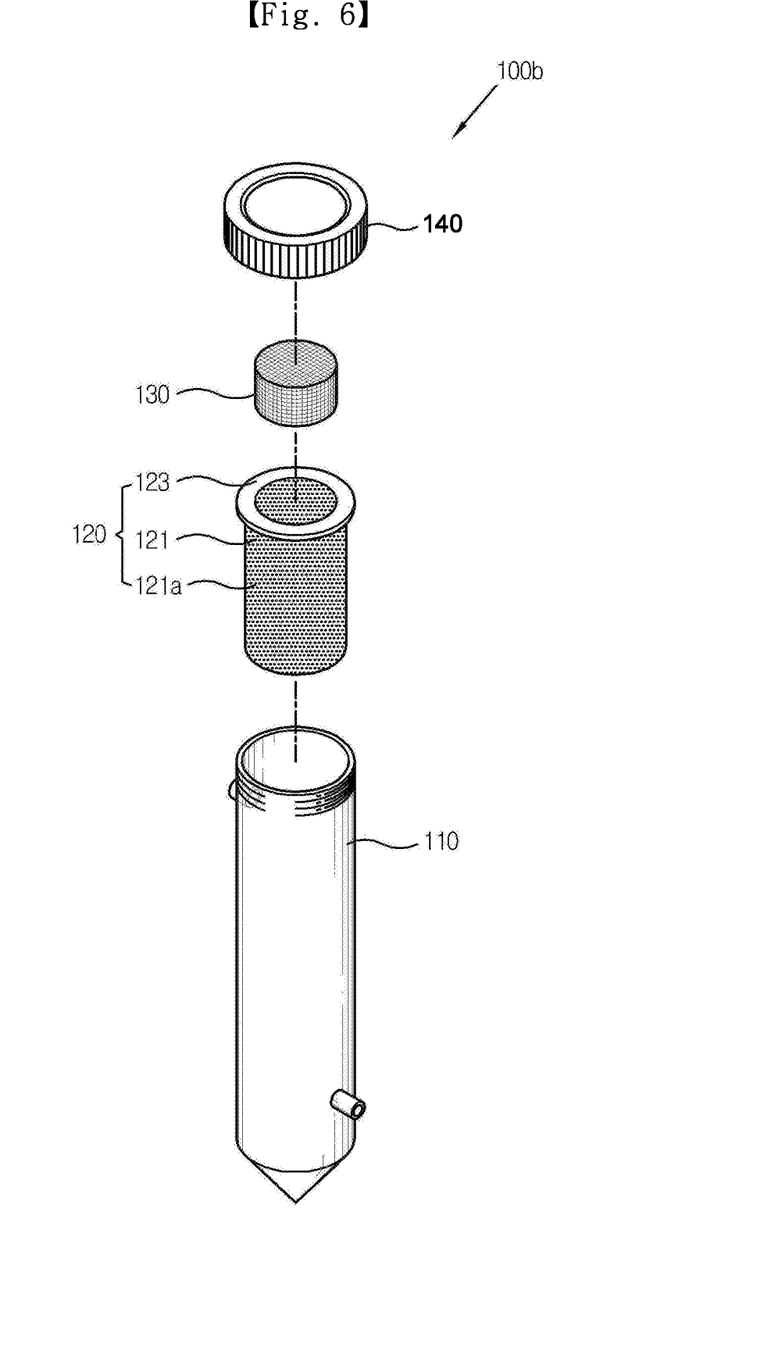
FIG. 6 is an exploded perspective view illustrating a constitution of a simple animal cell culture device according to yet another embodiment of the present disclosure.

Meanwhile, FIG. 6 is an exploded perspective view illustrating a constitution of a simple animal cell culture device 100b according to yet another embodiment of the present disclosure. While the simple animal cell culture devices 100, 100a according to the two embodiments described above have inlets 143 formed in the cover 140 to allow carbon dioxide to be introduced therethrough, the simple animal cell culture device 100b according to yet another embodiment does not have inlets 143. In this case, pH of the culture medium may be adjusted by adding carbonate ions to the medium being introduced through the medium introducing pipe 113. The effect is same as the two embodiments described above, because the carbonated solution with carbon dioxide dissolved therein is introduced along with the medium to adjust pH of the culture medium. In this case, because the inlet for carbon dioxide is omitted, ingress of various external germs is prevented basically, which in turn allows omission of another configuration such as the antibacterial filter 150.

The foregoing embodiments and advantages are merely exemplary and are not to be construed as limiting. The present teaching can be readily applied to other types of apparatuses. Also, the description of the embodiments is intended to be illustrative, and not to limit the scope of the claims, and many alternatives, modifications, and variations will be apparent to those skilled in the art.

The invention claimed is:

1. A simple animal cell culture device, comprising:
a culture vessel for holding a culture medium;
an animal cell reservoir coupled to an upper portion of the culture vessel;
a cell support housed inside the animal cell reservoir and to which animal cells are adhered; and
a cover for covering the upper portion of the culture vessel,
wherein the culture vessel is formed as a pipe of a predetermined length, and a first screw thread is provided on an outer circumference of an upper area of the culture vessel, wherein the animal cell reservoir comprises:

a reservoir body for housing the animal cells therein; and a coupling frame extending on an upper portion of the reservoir body externally in a radial direction, and locked with the upper portion of the culture vessel, wherein a second screw thread is provided on an inner side surface of the cover, for screw-coupling with the first screw thread, and wherein nutrient ingredients within the culture medium which is held in the culture vessel outside the animal cell reservoir, flows into an inside of the animal cell reservoir through an outer wall of the animal cell reservoir having semi-permeable property, and then the nutrient then reaches the cell support and contacts the animal cells.

2. The simple animal cell culture device of claim 1, wherein the animal cell reservoir is so formed that the animal cells and proteins therein are not allowed to be discharged outside, while nutrient ingredients and waste are allowed to be discharged outside.

3. The simple animal cell culture device of claim 2, wherein the animal cell reservoir is formed of any one of semi-permeable film, mesh net, non-woven fabric material and woven fabric material.

4. The simple animal cell culture device of claim 1, wherein the animal cell reservoir is so formed that the animal cells therein are not allowed to be discharged outside, while proteins, nutrient ingredients and waste are allowed to be discharged outside.

5. The simple animal cell culture device of claim 1, wherein a plurality of micro holes are pierced through a plate surface of the reservoir body, to allow the culture medium to be introduced and discharged therethrough.

6. The simple animal cell culture device of claim 1, wherein a medium introducing pipe extends from a lower portion of the culture vessel to a predetermined length, to allow a medium to be introduced from outside therethrough.

7. The simple animal cell culture device of claim 6, wherein a culture medium discharge pipe extends from the upper portion of the culture vessel to a predetermined length, to allow the culture medium to be discharged from inside to outside.

8. The simple animal cell culture device of claim 1, wherein an inlet is pierced through a surface of the cover to allow carbon dioxide to be introduced therethrough into the culture vessel.

9. The simple animal cell culture device of claim 8, wherein an antibacterial filter is provided between the cover and the culture vessel to remove germs contained in the carbon dioxide introduced through the cover.

10. The simple animal cell culture device of claim 1, wherein the cell support is formed as a lattice-shaped porous structure.

11. The simple animal cell culture device of claim 10, wherein the cell support is formed as a three-dimensional structure.

12. The simple animal cell culture device of claim 1, wherein a lower area of the culture vessel is formed as a conical shape.

13. The simple animal cell culture device of claim 1, wherein the cell support is formed as a three-dimensional structure consisting of a lateral support, a vertical support and a perpendicular support which are in orthogonal relations to each other.

14. An animal cell culture method, comprising:

filling the culture vessel of the simple animal cell culture device of claim 1 with the culture medium; and settling the cell support with the animal cells adhered thereto in the animal cell reservoir, for culture thereof.

15. The animal cell culture method of claim 14, wherein, according to elapse of an animal cell culture time, the culture vessel cover is opened and the culture medium is changed, repeatedly.

16. An animal cell culture method, comprising:

filling the culture vessel of the simple animal cell culture device of claim 7 with the culture medium; and settling the cell support with the animal cells adhered thereto in the animal cell reservoir, for culture thereof.

17. The animal cell culture method of claim 16, wherein, according to elapse of an animal cell culture time, the culture medium is changed repeatedly, by use of the medium introducing pipe and the culture medium discharge pipe.

18. An animal cell culture method, comprising:

filling the culture vessel of the simple animal cell culture device of claim 8 with a medium; and settling the cell support with the animal cells adhered thereto in the animal cell reservoir, for culture thereof.

19. The animal cell culture method of claim 18, wherein the culture medium is adjusted in pH thereof, as carbon dioxide is supplied through the inlet formed in the cover of the culture vessel.

* * * * *